(12) United States Patent
Smith

(10) Patent No.: US 8,535,365 B2
(45) Date of Paten: Sep. 17, 2013

(54) MOXA BURNING BOWL

(76) Inventor: Scott R. Smith, Erdenheim, PA (US)

( * ) Notice: Subject to any disclaimer, the term of this patent is extended or adjusted under 35 U.S.C. 154(b) by 442 days.

(21) Appl. No.: 13/021,212

(22) Filed: Feb. 4, 2011

(65) Prior Publication Data
US 2012/0203057 A1  Aug. 9, 2012

(51) Int. Cl.
*A61H 39/06* (2006.01)
*A61F 7/00* (2006.01)

(52) U.S. Cl.
USPC .......................................................... 607/114

(58) Field of Classification Search
USPC .......................................................... 607/114
See application file for complete search history.

(56) References Cited

U.S. PATENT DOCUMENTS

| | | | | |
|---|---|---|---|---|
| 4,604,088 A | * | 8/1986 | Nottbohm | 604/24 |
| 4,671,788 A | * | 6/1987 | Wu | 604/24 |
| 5,632,768 A | * | 5/1997 | Shimada | 607/96 |
| 2013/0018443 A1 | * | 1/2013 | Lee | 607/114 |

FOREIGN PATENT DOCUMENTS

| | | | |
|---|---|---|---|
| WO | WO 2004056304 A1 | * | 7/2004 |
| WO | WO 2007024060 A1 | * | 3/2007 |

* cited by examiner

*Primary Examiner* — Linda Dvorak
*Assistant Examiner* — Kaitlyn Smith
(74) *Attorney, Agent, or Firm* — Paul & Paul

(57) ABSTRACT

A moxa burning bowl is provided for application of heat treatment to body portions of a user, with the bowl having a flexible ring-shaped base member of a flexible cloth-like exterior and granular material therein, shaped in a ring-like or torus-like configuration, and having a generally concave shaped upper dish-like member and an open bottom, defining a zone therebetween when the bowl is placed on an exterior surface of a patient/user, for treatment. Moxa sticks or cones are carried by the dish-like member, projecting upwardly therefrom, and situated in sockets of the dish-like member, with the dish-like member having an upstanding periphery, enabling the dish-like member to catch fallen ash from burning moxa sticks or cones carried by the bowel.

5 Claims, 2 Drawing Sheets

MOXA BURNING BOWL

BACKGROUND OF THE INVENTION

Practitioners of acupuncture and of alternative medicine of various types often practice moxibustion to provide warmth to various regions of the body of a person, and most particularly to those portions of the body having acupuncture points, in order to stimulate circulation through acupuncture points and induce a smoother flow of blood. In such practice, moxa, generally a mugwort herb, is burnt to create heat and fumes that are applied near the skin, often at regions of the skin beneath which acupuncture points exist. The moxa generally come in the form of a elongate cylindrical structures that are sometimes somewhat conically shaped, and, regardless of shape, are often called cones or sticks.

Treatment by moxa can be used on its own, or in conjunction with acupuncture treatment.

In the prior art there have been developed moxa burning bowls that are generally shaped as an inverted bowl, with the bottom open to be applied over a body part of a patient/user, with the bowl often being cylindrical with a substantially closed top, except that the substantially closed top may have a plurality of sockets for receipt therein of moxa cones or sticks, with the bottoms of the cones or sticks engaged in the sockets, and with the cones or sticks being upstanding therefrom, with upper ends of the sticks being lit.

The thus lit moxa creates heat and fumes that traverse downwardly through the upstanding cones or sticks, into the interior of the inverted moxa bowl, exposing the surface of the skin of the user to which the bowl is applied to experience reception of heat and/or fumes from the burning moxa. Generally, the lower peripheral edge of the inverted moxabowl has some level of seal, to prevent escape of substantial amounts of heat and/or fumes.

A disadvantage of currently known prior art moxa burning bowls is that they are often difficult to safely overly portions of the body of a user that are not flat. For example, if a burning moxa bowl is applied to the irregular surface of the back of a hand, portions of a foot, an abdomen, a knee or the like, where such surfaces are not flat, not only will substantial amounts of heat and/or fumes from burning moxa escape where the lower end of the moxa bowl does not seal against the skin of the user, but the irregular surface of the skin of a user may make the moxa bowl sit unstably on the skin of a user, wobbling, and potentially falling off the location of the body part of the user to which it is to be applied. Also, because the burning moxa cones or sticks will ordinarily be hot at their upper, lit ends, the instability of a moxa burning bowl may pose serious burning risks to the patient or user, to which the treatment is being applied, for example because of a hot moxa cone or stick dropping off onto the skin of a patient, possibly causing a burn that could be as much as a second degree burn.

Accordingly, prior art moxa burning bowls often limit where on the surface of a patient the treatment can safely be applied.

Accordingly, with prior art moxa burning bowls, not only is there possibly a decrease in the effectiveness of the moxa treatment, but risk of burn to the patient because of an unbalanced bowl may impose a danger to the patient.

Such dangers can also be experienced when a burning moxa bowl is applied, for example, to the abdomen of a patient, in the event that the patient coughs or gives a sudden movement, and the above-discussed adverse conditions can be experienced.

SUMMARY OF INVENTION

The present invention provides a moxa burning bowl for treatment of bodily portions of a user by providing a flexible ring-shaped base member that is adapted to conform to the various portions of the body of a user/patient to which it may be applied, leaving a generally cylindrical open center for heat and/or moxa fumes to treat the patient, and wherein at the upper end of the flexible ring-shaped base member there is provided a dish-like member carried thereby and secured to the base member, with the dish-like member having a plurality of sockets for disposition of upstanding moxa sticks therein, and wherein the dish-like member has a generally concave upper surface whereby ashes from burning moxa sticks may fall onto such upper surface.

Accordingly, it is an object of the present invention to achieve the objects set forth above in the summary of invention.

It is a further object of this invention to accomplish the above object, wherein the flexible ring-shaped base member has a flexible ring-shaped exterior, that is substantially filled with granules or particles of sufficiently small size that allow the base member to conform to any body portion of a user to which the moxa burning bowl is to be applied, creating a generally enclosed heat/fume zone inside the ring-shaped base member between the dish-like member and the portion of the body of a user to which the moxa burning bowl is applied.

BRIEF DESCRIPTION OF THE DRAWING FIGURES

DETAILED DESCRIPTIONS OF THE PREFERRED EMBODIMENTS

Figure 1:
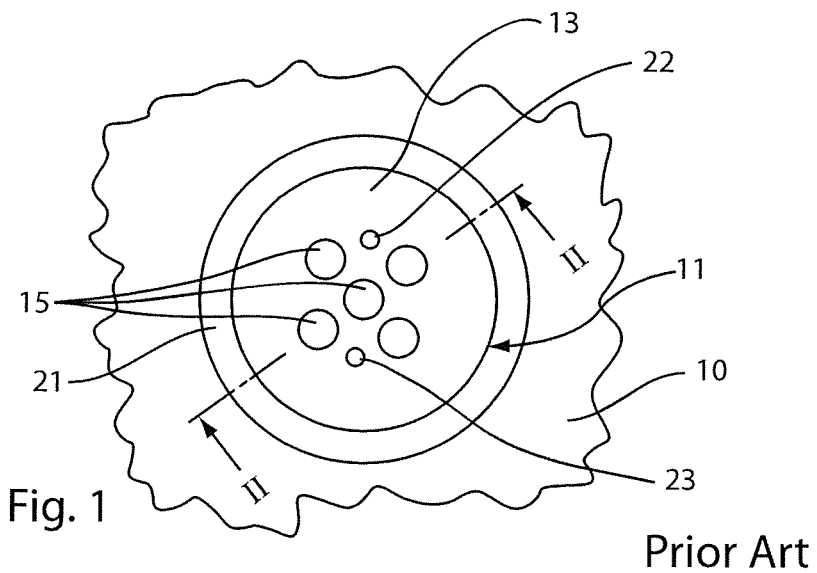
FIG. 1 is a top plan view of a moxa burning bowl applied onto the surface of a body portion of a patient/user, which body portion is fragmentally shown, and wherein the moxa burning bowl is of a prior art type.
Figure 2:
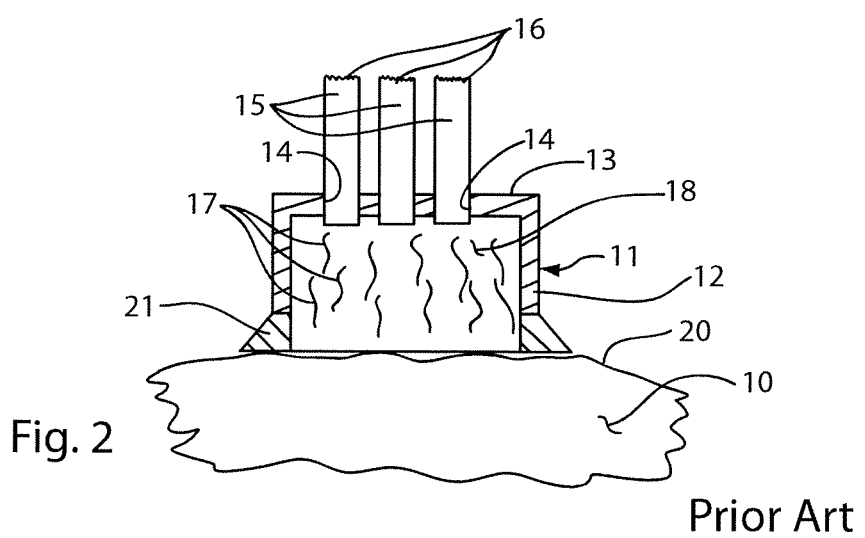
FIG. 2 is a vertical sectional view taken through the moxa burning bowl of FIG. 1, generally along the line II-II of FIG. 1, and wherein the heat/fume zone between the inverted moxa burning bowl and the skin of a patient/user is shown, with upstanding moxa sticks or cones projecting upwardly from the moxa burning bowl, also illustrating the prior art.

Referring now to the drawings in detail, reference is first made to FIG. 1, wherein a portion of the skin of a body part of a patient is fragmentally illustrated at 10. A moxa burning bowl 11 is provided, in the shape of a bowl that is inverted over the body part 10 of a patient, and comprises a cylindrical sidewall 12, with a top 13, with a plurality (5 shown) of sockets 14 therein, with a moxa stick or cone 15 disposed in each socket 14. The moxa sticks or cones 15 have been lit at their upper ends 16 to burn, creating fumes and heat illustrated at 17, in the zone 18 between the top 13 and surface 20 of the body of a user to which the moxa burning bowl 11 is applied. Openings 22 and 23 from above the top 13 to the zone 18 therebeneath allow an exchange of air between a zone above the moxa bowl and the zone 18, enabling the burning moxa sticks to pass heat and fumes to the zone 18.

At the bottom of the cylindrical portion 12 of the moxa burning bowl 11, there is provided a peripheral seal 21 that may, if desired, be of a conformable material such as rubber, neoprene, or any other material that may help to seal the moxa burning bowl 11 against the surface 20 of the patient/user to which it is applied.

Figure 3:
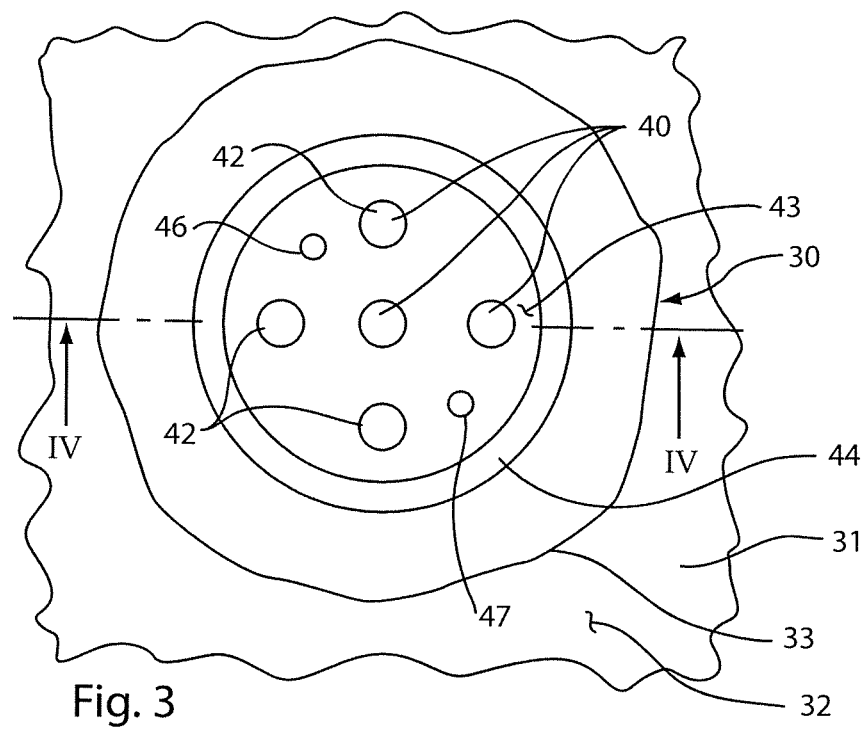
FIG. 3 is an illustration somewhat similar to that of FIG. 1, but wherein the moxa burning bowl in accordance with this invention is illustrated, disposed on a fragmentary portion of the body of a patient/user to which it is applied.
Figure 4:
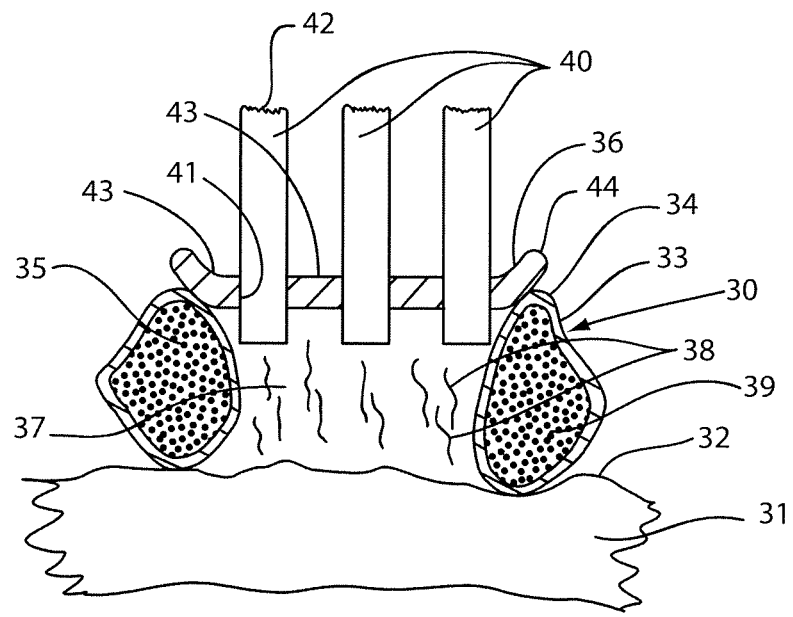
FIG. 4 is a vertical sectional view taken through the moxa burning bowl of FIG. 3, generally along the line IV-IV of FIG. 3, and wherein the conformability of the ring-shaped base member comprised of a flexible outer material containing granules therein may conformably be applied to irregular surfaces of the body of a patient.

Referring now to FIGS. 3 and 4, the moxa burning bowl 30 of this invention is illustrated applied onto a body part 31 of a patient, the surface 32 of which is irregular.

The moxa burning bowl 30 includes a flexible ring-shaped member 33 comprised of a flexible material 34 that is torus-shaped or ring-shaped, as shown, having a hollow interior 35, that is filled with granules of sufficiently small size particles that enable the base member 33 to conform to the irregular surface 32 of a body part 31 of a user, such that the combination of the granular material 39 inside the base member 33 and the flexible exterior 34 of the base member 33 create an effective seal between a dish-like member 36 mounted on and secured to the base member 33 at its upper end, creating a heat and vapor treatment zone 37 between the dish-like member 36 and the surface 32 of the patient/user, whereby fumes 38 from upstanding moxa cones or sticks 40 disposed in sockets 41 of the dish-like member 36 may flow to the patient 31. The cones or sticks 40 are lit at their upper ends, as shown at 42, whereby the treatment heat and vapors may be applied to the upper surface 32 of the body part 31 of the patient/user by traversing downwardly through the cones or sticks 40 (used interchangeably herein), into the zone 37, creating the fumes and/or heat 38 that effect the treatment of the patient/user. The small holes 46, 47 between the area above the dish-like member 36 and the zone 37, allow an exchange of air between a zone above the dish-like member 36 and the zone 37, allowing moxa fumes and heat into zone 37.

It will be noted that the dish-like member has a generally concave upper surface 43 as shown, terminating in an upstanding peripheral edge 44, such that hot ashes from the burning cones or sticks 40 may be collected on the concave surface 43 of the dish-like member 36, and not fall onto the body portion 31 of a patient/user, as may possibly occur with moxa burning bowels of the prior art type.

The granules 35 of the ring-shaped base member 30 may comprise any particles that will accomplish the conformability purposes of the base member 33, and such can include small pebbles, various types of seeds, grains of sand, or any other free-flowing particulate material that would not be prone to or adapted to solidify it into a single mass in the torus-shaped or ring-shaped interior of the base member. The exterior 34 of the ring-shaped base member may be comprised of any suitable flexible material that will conform to an irregular surface 32 of a body part 31 of a patient/user, and materials for the same may include cloth, flexible plastic materials, rubber-like materials, or any other flexible sheet-like material that is adapted to the purposes of this invention.

The moxa burning bowl of this application can be made in various sizes to accommodate different portions of the body of a user/patient, as well as to accommodate patients of different sizes. Thus, the ring-shaped based member may be made such that its zone 37 can be made to have any desired diameter. The dish-shaped member 36, carried thereby can likewise, if desired, be made to be of different diameters to provide heat and fumes to differently sized portions of the body of a user/patient.

It will be apparent from the foregoing that various modifications may be made in the details of construction, as well as in the use and operation of the moxa burning bowl in accordance with this invention as defined by the appended claims.

What is claimed is:

1. A moxa burning bowl for application of heat and/or fume treatment of bodily portions of a user by supporting lit moxa sticks above a moxa heat and/or fume application zone adjacent a bodily portion of a user, comprising:
    (a) a flexible ring-shaped base member adapted to be applied to a portion of a body of a user; with the base member including means conforming a bottom of the base member to at least irregular non-flat surfaces on the body of a user, leaving an open center of the ring-shaped base member open to the surface of a body portion of the user;
    (b) a dish-like member carried by an upper end of the base member;
    (c) the dish-like member having a plurality of sockets for disposition of upstanding moxa sticks in said sockets; and
    (d) with the dish-like member having a generally concave upper surface as viewed from above when the bowl is disposed on a body portion of a user, whereby the generally concave upper surface of the dish-like member may receive fallen ashes from burning moxa sticks.

2. The moxa burning bowl of claim 1, wherein the ring-shaped base member includes a generally hollow ring-shaped exterior having a generally torus-shaped interior, wherein the torus-shaped interior contains granules of sufficiently small particles that enable the base member to conform to the body portion of a user to which the base member is applied, creating a generally enclosed heat/fume zone inside the ring-shaped base member between the dish-like member and the portion of the body of a user to which the moxa burning bowl is applied.

3. The moxa burning bowl of claim 2, wherein said granules comprise any of:
    (i) pebbles;
    (ii) particles of seed;
    (iii) grains of sand; and
    (iv) any other free-flowing particulate material not adapted to solidify into a single mass in the torus-shaped interior of the ring-shaped base member.

4. The moxa burning bowl of claim 2, wherein the ring-shaped exterior of the base member comprises any of:
    (i) cloth material;
    (ii) flexible plastic material;
    (iii) rubber-like material; and
    (iv) any flexible sheet-like material.

5. The moxa burning bowl of claim 3, wherein the ring-shaped exterior of the base member comprises any of
    (i) cloth material;
    (ii) flexible plastic material;
    (iii) rubber-like material; and
    (iv) any flexible sheet-like material.

\* \* \* \* \*